US00PP15874P2

(12) United States Plant Patent
Olesen et al.

(10) Patent No.: US PP15,874 P2
(45) Date of Patent: Jul. 19, 2005

(54) ROSE PLANT NAMED 'POULAC016'

(50) Latin Name: *Rosa hybrida*
Varietal Denomination: POULac016

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,795

(22) Filed: Dec. 16, 2003

(51) Int. Cl.[7] ..... A01H 5/00
(52) U.S. Cl. ..... Plt./150
(58) Field of Search ..... Plt./150, 151, 108, Plt./139

*Primary Examiner*—Anne Marie Grunberg
*Assistant Examiner*—June Hwu

(57) ABSTRACT

A new compact floribunda rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULac016'.

SUMMARY OF THE INVENTION

The present invention constitutes a new and distinct variety of floribunda rose plant which originated from a controlled crossing between a female parent plant, an unnamed seedling, and the male parent, 'POULra007', a plant created by the same inventors, described and illustrated in U.S. Plant Pat. No. 13,170 dated Nov. 5, 2002. The two parents were crossed and the resulting seeds were planted in a controlled environment. The new variety is named 'POULac016'.

The new rose may be distinguished from its seed parent by the following combination of characteristics:

1. The seed parent has a red and yellow flower color. The same of 'POULac016' is Red-Purple Group 57A.
2. The seed parent has a petal count of 15 to 20 petals. 'POULac016' has a petal count of 100 petals.

The new variety may be distinguished from its pollen parent, 'POULra007', by the following combination of characteristics:

1. The pollen parent has a flower bud color of Red-Purple Group 59A. The same of 'POULac016' is Purple Group 57A.
2. Average flower diameter of the pollen parent is 50 mm when open. Average flower diameter of 'POULac016' is 40 mm.
3. 'POULra007' has 40 to 50 petals. 'POULac016' has 100 petals on average.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULac016' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULac016' was selected by the inventors as a single plant from the progeny of the hybridization in 2000.

Asexual reproduction of 'POULac016' by cuttings and traditional budding was first done by L. Pernille and Mogens N. Olesen in their nursery in Fredensborg, Denmark in Spring 2000. This initial and other subsequent propagations conducted in controlled environments have demonstrated that the characteristics of 'POULac016' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULac016'. Specifically illustrated in the drawing:

FIG 1.1; Open flower;

FIG 1.2; Flower bud at various stages of development;

FIG 1.3; Sepals, receptacle, and pedicel;

FIG 1.4; Flower petals, detached;

FIG 1.5; Mature lef and juvenile leaves; depicting anthocyanic pigment coloration;

FIG 1.6; Bare stem exhibiting thorns.

DETAILED DESCRIPTION OF THE VARIETY

The following is a description of 'POULac016', as observed in its growth in a glasshouse located in Burlington, Canada. Observed plants are 3 months of age, grown in 15 cm pots. Color references are made using The Royal Horticultural Society (London, England) Colour Chart, 1995, except where common terms of color are used.

For a comparison, several physical characteristics of the rose variety 'POULsabel', a rose variety from the same inventors described and illustrated in U.S. Plant patent application No. 10/136,451 dated Apr. 29, 2002, now abandoned, is compared to 'POULac016' in Chart 1.

CHART 1

| | 'POULac016' | 'POULsabel' |
|---|---|---|
| General tonality | Red-Purple Group 57A | Red Group 53A |
| Petalage | 100 petals. | 30 to 35 petals. |
| Bloom diameter | 46 mm. | 55 mm. |

FLOWER AND FLOWER BUD

Blooming habit: Continuous.

Flower bud:

*Size.*—Upon opening, 18 mm in length from base of receptacle to end of bud.

*Bud form.*—Globular.

*Bud color.*—As sepale unfold, Red Group 53A; Red Group 46A to Red-Purple Group 57A at ¼ opening.

*Sepals.*—Upper Surface: Color: Yellow-Green Group 146A. Surface: Slightly pubescent. Lower Surface: Color: Yellow Green Group 146B. Shape: Sepal apex is cirrhose. Base is flat at union with receptacle. Margins: Very strong foliaceous appendages on three of the five sepals. Size: 40 mm (l) ×13 mm (w).

*Receptacle.*—Shape: Funnel shaped. Size: 4 mm (h)×6 mm (w). Color: Yellow Green Group 144B. Anthocyanin: None observed.

*Peduncle.*—Surface: Smooth with stipitate glands. Length: 75 mm to 85 mm average length. Color: Yellow-Green Group 144B. Strength: Very strong.

*Anthocyanin.*—None observed.

*Borne.*—Singularly.

Flower bloom:

*Fragrance.*—Light floral.

*Duration.*—As a pot plant, flowers last from 10 to 14 days.

*Size.*—Average flower diameter is 46 mm when open.

*Form.*—Shape of flower when viewed from the side: Upon opening, upper part: Flat. Upon opening, lower part: Concave. Open flower, upper part: Convex. Open flower, lower part: Concave.

*Petalage.*—100 petals under normal conditions. 15 petaloids on average.

Color:

*Upon opening, petals.*—Outermost petals: Outer Side: Red-Purple Group 57A. Inner Side: Red-Purple Group 57A. Innermost petals: Outer Side: Red-Purple Group 57A. Inner Side: Red-Purple Group 57A.

*Upon opening, basal petal spots.*—Outermost petals: Outer Side: White Group 155 B to Yellow Group 4D. Inner Side: White Group 155 B to Yellow Group 4D. Innermost petals: Outer Side: White Group 155 B to Yellow Group 4D. Inner Side: White Group 155 B to Yellow Group 4D.

*After openng, petals.*—Outermost petals: Outer Side: Red-Purple Group 57A. Inner Side: Red-Purple Group 57A. Innermost petals: Outer Side: Red-Purple Group 57A. Inner Side: Red-Purple Group 57A.

*After opening, basal petal spots.*—Outermost petals: Outer Side: White Group 155 B to Yellow Group 4D. Inner Side: White Group 155 B to Yellow Group 4D. Innermost petals: Outer Side: White Group 155 B to Yellow Group 4D. Inner Side: White Group 155 B to Yellow Group 4D.

General tonality: On open flower Red-Purple Group 57A. No change in the general tonality at the end of the $10^{th}$ day. Afterwards, general tonality is Red-Purple Group 57A to 57B.

Petals:

*Petal reflex.*—Petals reflex strongly.

*Petal margin.*—Entire.

*Shape.*—Base shape is acute. Apex shape is round.

*Size.*—25 mm (l)×22 mm (w).

*Thickness.*—Thick.

*Arrangement.*—Not formal.

Petaloids:

*Quantity.*—10 to 15.

*Size.*—11 mm (l)×5 mm (w).

*Shape.*—Elliptical and irregular.

*Color.*—Red Group 57A.

*Arrangement.*—Not formal.

Reproductive organs:

*Pistils.*—Length: 9 mm long. Quantity: 29 (actual count).

*Pollen.*—None observed. Flowers are incomplete.

*Anthers.*—None observed. Flowers are incomplete.

*Filaments.*—None observed. Flowers are incomplete.

*Stigmas.*—Color: Green-Yellow Group 160B.

*Styles.*—Color: Yellow-Green Group 145C.

*Seed formation.*—Not observed.

PLANT

Plant growth: Vigorous, compact, upright to bushy. When grown as a 15 cm pot plant, the average height of the plant itself is 25 cm and the average width is 17 cm.

Stems:

*Color.*—Young wood: Yellow-Green Group 144A. Older wood: Yellow-Green Group 144A.

*Internodal distance.*—20–40 mm.

*Surface texture.*—Young wood: Smooth. Older wood: Smooth.

Thorns:

*Incidence.*—7 mm per 10 cm of stem.

*Size.*—3 mm in length.

*Color.*—Juvenile and mature thorns are Yellow-Green Group 145C.

*Shape.*—Linear.

Plant foliage: Normal number of leaflets on normal leaves in middle of the stem: 5 leaflets.

*Compound leaf size.*—115 mm (l)×85 mm (w).

*Quantity.*—5 leaves per 10 cm of stem on average.

*Color.*—Juvenile foliage: Upper Leaf Surface is Green Group 137A to Yellow-Green Group 144A with anthocyanic pigment the color of Greyed-Purple Group 183B at the margins and veins. Lower Leaf Surface is Yellow-Green Group 146C to Yellow-Green Group 146B with anthocyanic pigment the color of Greyed-Purple Group 183B at the margins and veins. Mature foliage: Upper Leaf Surface is Green Group 137A to Yellow-Green Group 146A. Lower Leaf Surface is Yellow-Green Group 146C to Yellow Green Group 146B.

Plant leaves and leaflets:

*Stipules.*—Size: 5 mm in length. Color: Green Group 144A. Margins: Finely serrated with medium quantity of stipitate glands.

*Petiole.*—Length: 20 mm. Width: 1 mm. Color: Yellow-Green Group 144B. Underneath: Thorns and stipitate glands observed.

*Rachis.*—Size: 28 mm length. Color: Yellow-Green Group 144B. Underneath: Thorns and stipitate glands.

*Leaflet.*—Size: 45 mm (l)×29 mm (w). Edge: Serrated. General Shape: Ovate. Texture: Smooth. Thickness: Thick. Arrangement: Odd pinnate. Venation: Reticulate. Leaf Gloss: Moderately glossy finish.

Disease resistance: Average resistance to mildew, rust, black spot, and Botrytis under normal glasshouse growing conditions in Burlington, Canada.

It is claimed:

1. A new and distinct variety of rose plant of the compact floribunda class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

* * * * *

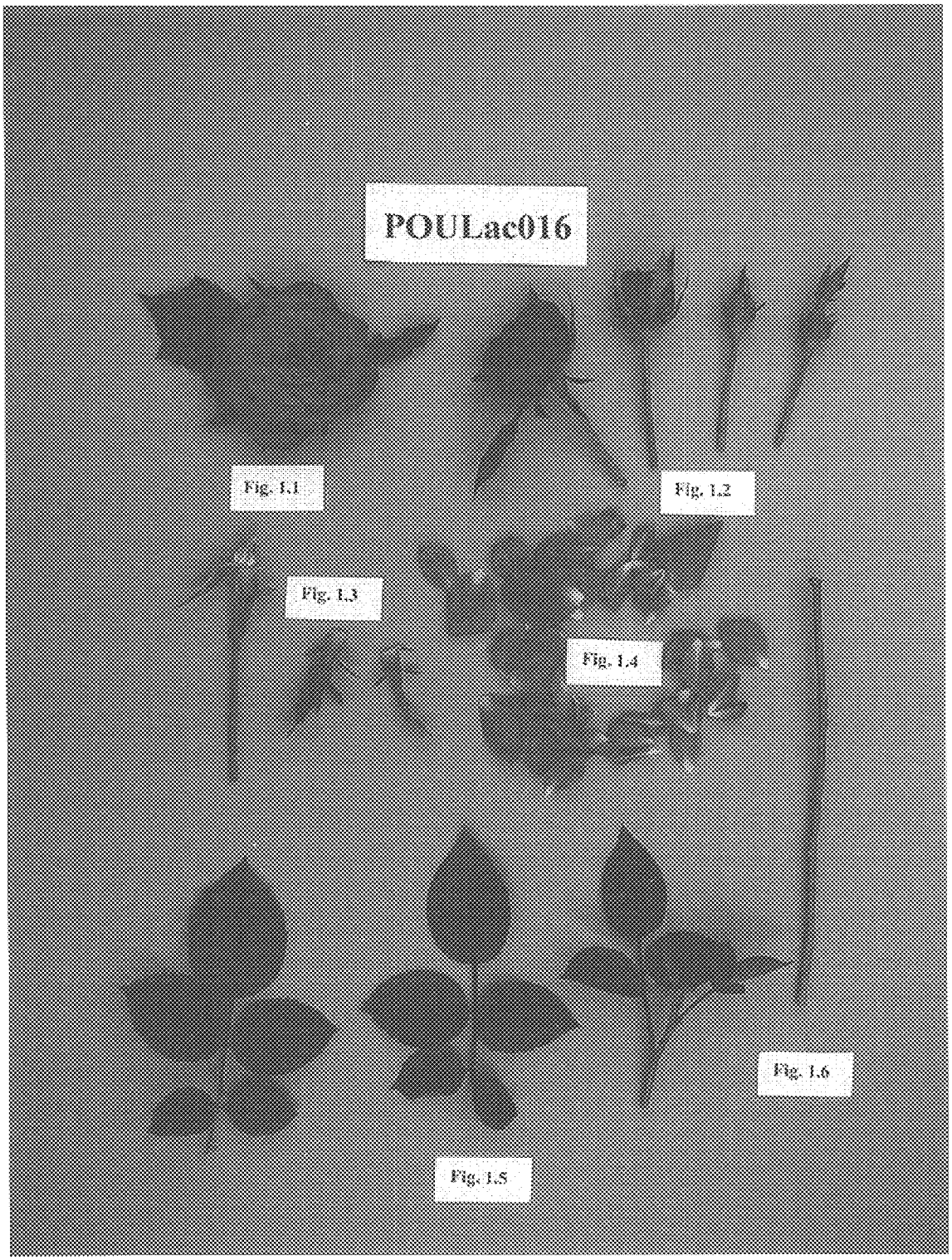
POULac016
Fig. 1.1
Fig. 1.2
Fig. 1.3
Fig. 1.4
Fig. 1.5
Fig. 1.6